US011885220B2

(12) United States Patent
Ramirez Sabag

(10) Patent No.: US 11,885,220 B2
(45) Date of Patent: Jan. 30, 2024

(54) SYSTEM TO DETERMINE EXISTING FLUIDS REMAINING SATURATION IN HOMOGENOUS AND/OR NATURALLY FRACTURED RESERVOIRS

(71) Applicant: Instituto Mexicano del Petróleo, Mexico City (MX)

(72) Inventor: Jetzabeth Ramirez Sabag, Mexico City (MX)

(73) Assignee: Instituto Mexicano del Petróleo, Mexico City (MX)

(*) Notice: Subject to any disclaimer, the term of this patent is extended or adjusted under 35 U.S.C. 154(b) by 0 days.

(21) Appl. No.: 18/198,067

(22) Filed: May 16, 2023

(65) Prior Publication Data

US 2023/0304399 A1    Sep. 28, 2023

Related U.S. Application Data

(62) Division of application No. 16/936,170, filed on Jul. 22, 2020, now Pat. No. 11,692,441.

(30) Foreign Application Priority Data

Jul. 23, 2019    (MX) .................... MX/a/2019/008720

(51) Int. Cl.
*E21B 43/20*    (2006.01)
*E21B 47/06*    (2012.01)
(Continued)

(52) U.S. Cl.
CPC ............ *E21B 49/088* (2013.01); *E21B 43/20* (2013.01); *E21B 47/06* (2013.01); *E21B 47/07* (2020.05);
(Continued)

(58) Field of Classification Search
CPC ........ E21B 47/11; E21B 49/088; E21B 47/06; E21B 43/20; E21B 43/26; E21B 49/00;
(Continued)

(56) References Cited

U.S. PATENT DOCUMENTS 2,806,372 A * 9/1957 Arps ...................... E21B 47/11
33/732
5,222,867 A * 6/1993 Walker, Sr. ........... E21B 47/009
417/63

(Continued)

FOREIGN PATENT DOCUMENTS

CA         2644452 A1 * 10/2007    ......... E21B 47/1015

*Primary Examiner* — Jeffrey P Aiello
(74) *Attorney, Agent, or Firm* — FisherBroyles, LLP; Jason P. Mueller

(57) ABSTRACT

An object of the disclosure is to determine the remaining saturation of existing fluids in naturally fractured and/or homogeneous reservoirs, considering an unconventional tracer test, using the double tracer test method with pressure monitoring (PDTcMP®), which also integrates unused technical elements, in order to estimate more accurately the value of the remaining oil saturation (ROS) in naturally fractured reservoirs, unlike conventional methods used most commonly in homogeneous media. The disclosure substantially modifies the conventional tracer test, as it uses innovative technical elements, which reduce the uncertainty and/or ambiguity associated with conventional tracer tests, when they are applied in naturally fractured reservoirs.

13 Claims, 7 Drawing Sheets

(51) Int. Cl.
*E21B 47/07* (2012.01)
*E21B 49/08* (2006.01)
*G01N 23/00* (2006.01)
*G01N 30/00* (2006.01)
*G01N 33/24* (2006.01)
*G01V 5/04* (2006.01)

(52) U.S. Cl.
CPC .............. *G01N 23/00* (2013.01); *G01N 30/00* (2013.01); *G01N 33/241* (2013.01); *G01V 5/04* (2013.01)

(58) Field of Classification Search
CPC ........ E21B 49/008; G01V 11/00; G01V 5/04; G01V 1/40; G01V 2210/646; G01N 23/00; G01N 30/00; G01N 24/081
USPC ....... 73/152.39, 152.46, 152.51; 166/250.01, 166/250.16, 252.1, 250.1, 252.6, 305.1; 340/853.1; 367/72, 25; 702/12, 13, 6, 8, 702/9, 2, 22; 703/9, 10
See application file for complete search history.

(56) References Cited

U.S. PATENT DOCUMENTS

| | | | |
|---|---|---|---|
| 2003/0178191 A1* | 9/2003 | Maher | E21B 43/24 166/65.1 |
| 2004/0020642 A1* | 2/2004 | Vinegar | E21B 47/0224 166/245 |
| 2007/0000663 A1* | 1/2007 | Kelley | E21B 43/168 166/268 |
| 2012/0230151 A1* | 9/2012 | Almaguer | E21B 7/061 166/241.1 |
| 2019/0203587 A1* | 7/2019 | Kulyakhtin | E21B 49/08 |

* cited by examiner

SYSTEM TO DETERMINE EXISTING FLUIDS REMAINING SATURATION IN HOMOGENOUS AND/OR NATURALLY FRACTURED RESERVOIRS

CROSS-REFERENCE TO RELATED APPLICATIONS

This patent application is a divisional of U.S. patent application Ser. No. 16/936,170, filed Jul. 22, 2020, which claims priority to Mexican Patent Application No. MX/a/2019/008720, filed Jul. 23, 2019, the entire disclosure of which is hereby incorporated by reference herein.

TECHNICAL FIELD

The present disclosure refers to a system that determines the remaining saturation of existing fluids in homogeneous and/or naturally fractured reservoirs, based on the use of tracers (radioactive and chemical), in order to quantify the volume of remaining oil found in the deposit area being studied.

BACKGROUND

Currently, most of the oil produced in the world comes from mature fields with more than 30 years of longevity, which focuses the interest of the oil industry in the development of such fields.

The economic success and technologies used to revitalize these mature fields are based on well applications or development practices that can help improve production. For any of the recovery processes, the first question that arises is the amount of remaining oil reserves and its distribution within the formation. Once these results are obtained, the appropriate recovery method or methods must be selected for each case, since their applicability in mature deposits will depend on the aid provided to increase recovery rates and the efficiency of the method (cost and time). Therefore, the determination of the remaining oil saturation, before and after production processes, is a major challenge today and even more so when it comes to naturally fractured reservoirs.

To date there are several techniques used to determine the remaining oil saturation: core analysis, well logs, volumetric studies, analysis of production data, pressure variation tests, etc. However, the results obtained from these methods may not be representative for the reservoir because the field scale displacement is not controlled only by microscopic factors; in addition, this estimation may be uncertain due to the pore size distribution or the heterogeneity of the nucleus.

Likewise, the remaining oil saturation values obtained in the laboratory may vary depending on the production rate, the type of sample, and the treatment given to said sample.

Tracer tests offer another way to determine remaining oil saturation, based on the following principle: when a chemical tracer is injected into the reservoir, its molecules are locally distributed between water and oil; these tracer molecules will move with a characteristic velocity that depends on the fraction of time they occupy in each phase. The velocity for each tracer is obtained from the field test and the partition coefficients of the laboratory. Also, when a tracer with a known partition coefficient is injected and the breakthrough time in another well is measured, it is possible to obtain the remaining saturation of oil.

Conventional single-well tracer tests utilized to determine remaining oil saturation (method proposed by Harry A. Deans, 1978) have been successfully applied to homogeneous type reservoirs. In this methodology, the determination of the remaining oil saturation is based on the fact that the breakthroughs of two tracers (one partitionable and the other non-partitionable) are presented at different times, which are related to the volume of oil in the formation. The basic premise of the method is that the delay in the response of the partitionable tracer is due to the fact that this tracer is very soluble in the oil phase and naturally seeks to change to the existing oil phase in the porous medium. Therefore, in the event that no oil is found in the formation, this tracer cannot be partitioned and will break at the same time as the non-partitionable tracer, thus the response delay is due to the amount of oil present in the study area. However, there are heterogeneities in the reservoir that increase the uncertainty of this type of tests, especially, in the case of naturally fractured reservoirs; by applying this same method, it will not be possible to differentiate if the delay in the response of the partitionable tracer is due to oil found in the matrix or oil found in fractures. While applying Harry A. Deans method, this would be the great unknown.

Based on the previous statements, developing methodologies that estimate the remaining oil saturation through tracer tests between wells, that allow gas and water zones to be admitted in naturally fractured reservoirs, still represent a challenge today.

The patents that precede the present invention are the following:

U.S. Pat. No. 3,623,842, Harry A. Deans, Method of determining fluid saturations in reservoir, describes a method for determining oil saturation in homogeneous reservoirs, where a reaction fluid carrier solution is injected into the formation through a well. The carrier fluid is insoluble in oil and miscible with formation water. The reagent forms at least one tracer (non-partitionable) within the array with different partition coefficients.

U.S. Pat. No. 3,902,362, John F. Tomich and Harry A. Deans, describes a method for measuring fluids and the mobile phase of saturation, disclosing a technique that determines relative amounts of fluids in underground formations, where one of the phases is mobile and the other is essentially immobile. In the mobile phase, a fluid drift occurs within the formation, due to the mix with formation fluids. Subsequently, two tracers having significantly different partition coefficients are injected. Once injected, the well is closed and the fluid carrying two traces is allowed to move within the formation. Due to the difference in the distribution or partition coefficients of the two tracers and to the mobility in the formation under the influence of the fluid, there will be a separation of the tracers using the chromatographic principle. Fracture effects in the medium is not considered in this patent.

U.S. Pat. No. 4,102,396, Robert C. Ransom, describes a method for determining the remaining oil saturation after injection. This patent discloses a method of determining fluid saturation with a measurement technique after a secondary recovery operation. In the operation, hydrocarbons or gas are injected.

All the previous patents focus on formations with homogeneous behavior, where there is no fluid drift; so that if it was present, this type of method would not be successful, since it would not be possible to recover the sufficient and statistically representative tracer to obtain the oil saturation.

Mexican patent MX346226 (B) by Jetzabeth Ramirez Sabag et al., describes a tracer measurement equipment, which connects to the oil well discharge line and measures the concentration of tracers present on the well production line in real time.

The previous patent bibliography reported by the applicant represents totally different applications from the one described in the present disclosure, by virtue of the fact that a method that allows the user to estimate the remaining oil saturation in both naturally fractured and homogeneous, considering the participation of the matrix and present fractures, is provided in the instant disclosure.

Therefore, one of the objects and advantages of the present disclosure is to provide the user with a highly certain method to estimate the remaining oil saturation in fields invaded by water, in both, naturally fractured reservoirs and reservoirs with homogeneous behavior, in order to achieve a quantification of remaining oil as close to reality. The foregoing, through innovative elements additional to those considered by prior methods, which significantly reduce the uncertainty related to: the channeling of injection fluids (including tracers) as well as the fluid drift that occurs in formations with heterogeneous behavior.

Another object of the present disclosure is to statistically obtain representative data, in addition to prior methods, such as: four tracer responses (two radioactive and two chemical) at the location of the well, as well as the well pressure measurement study. These additional elements, when analyzed and interpreted together, determine the remaining oil saturation, including both the matrix and the fracture effects, in the case of naturally fractured reservoirs, as well as the flow regimes associated with the field test; it is also possible to determine some properties of the rock-fluid system that complement the information from the tracer test to determine the remaining oil saturation, such as formation porosity.

Yet another object of the present disclosure is to provide an innovative method that integrates the data obtained with radioactive and chemical tracers, as well as the background pressure log, at the well location. This implies time and cost savings, in addition to the sensitivity of the results, meaning, it allows the optimization of the test design of the partitionable tracers on site. Everything described above significantly reduces the probability of failure of the same test.

BRIEF DESCRIPTION OF THE DRAWINGS OF THE INVENTION

FIG. 1 schematically shows Phase 1 of the previous "mini-test" method, in order to experience the formation response before using the partitionable tracers, where said "mini-test" consist of the injection of a radioactive tracer gamma emission diluted in water of formation (point A), of the shutdown of the well (point B) and the opening of the well to production (point C), being the product in which the concentration of the injected tracer (radioactive, non-partitionable, continuous, and in well discharge line) is measured.

Figure 5:
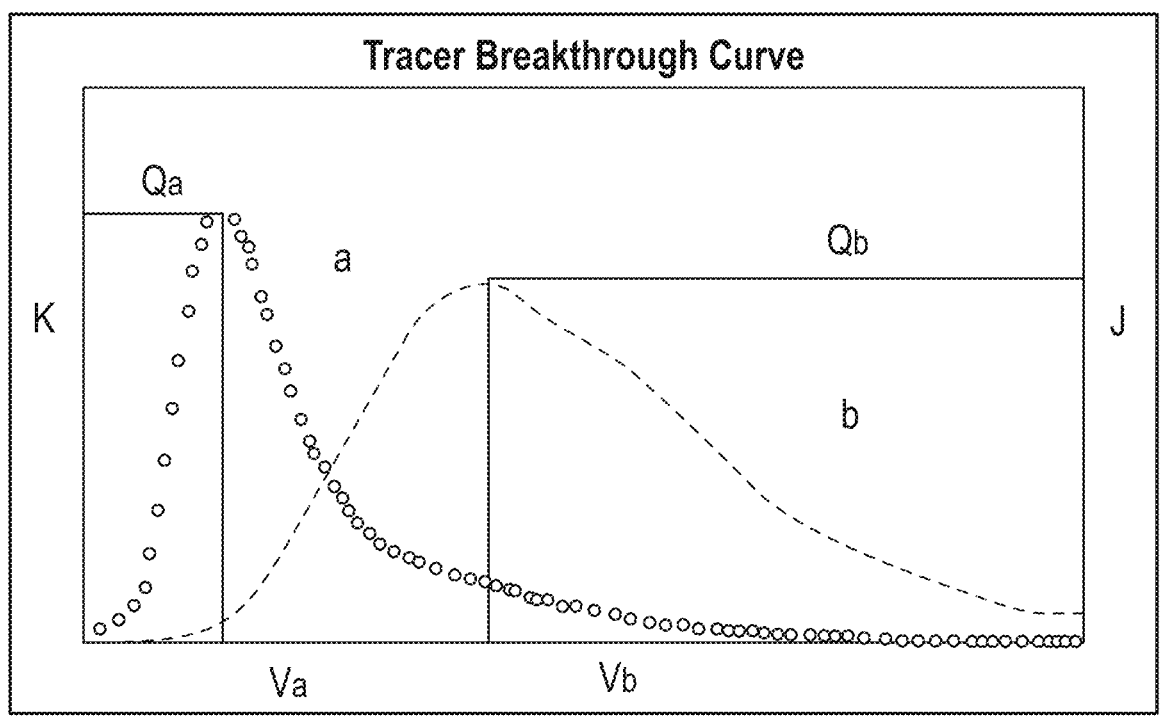

FIG. 5 shows the chemical tracers' breakthrough curves: a, is the non-partitionable tracer (product of hydrolysis); b, the partitionable (primary) tracer; Vb, indicates the volume produced of the partitionable tracer; Va, is the produced volume of the non-partitionable tracer; K (left axis) represents the concentration of the tracer product of the hydrolysis reaction in ppm; and, J, (right axis), the concentration of the primary tracer in ppm, both measured in the effluent from the well.

Figure 6:
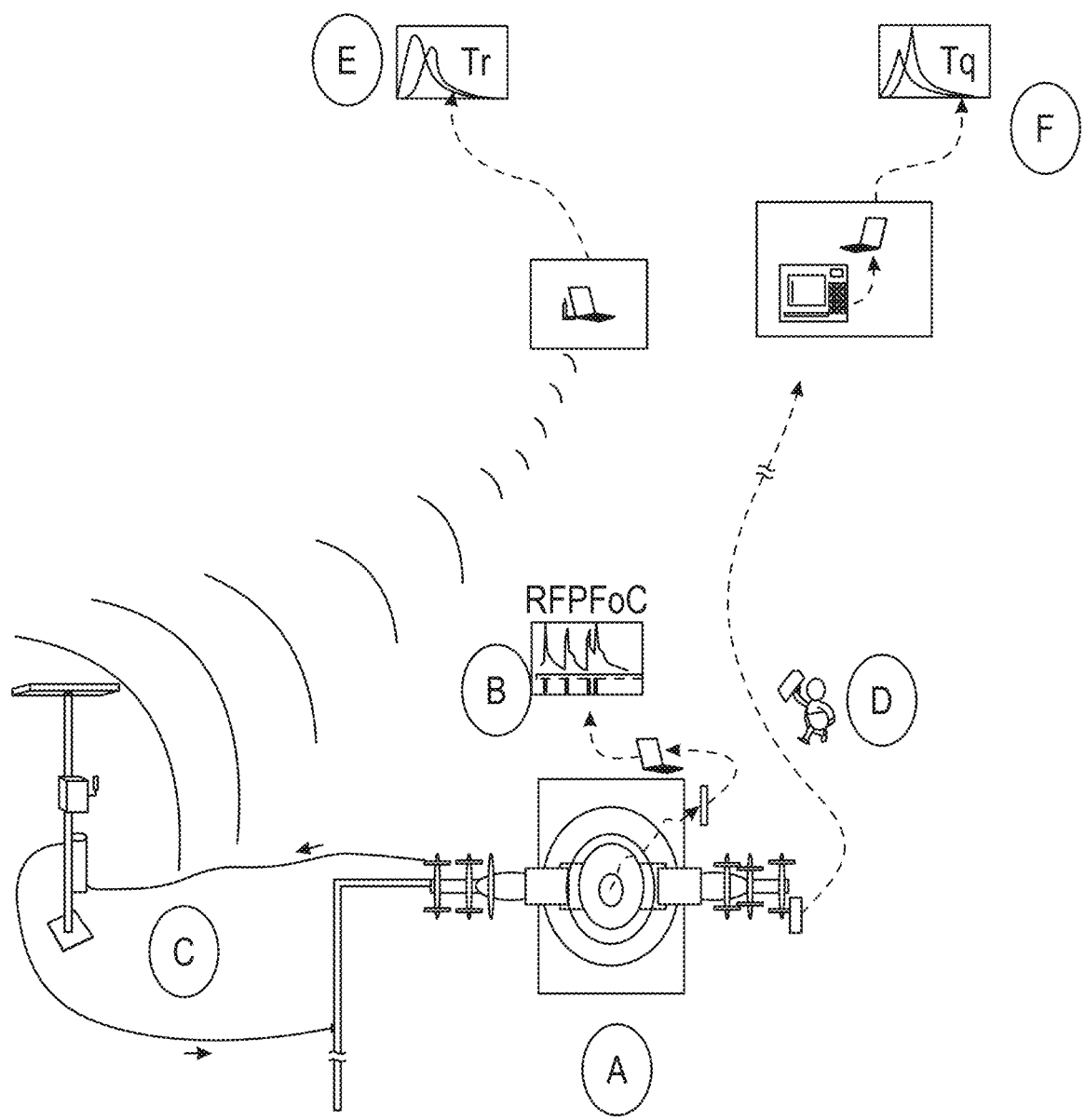

FIG. 6 illustrates the plan system of the present invention PDTcMP®: point A represents the wellhead under study with two branches (it does not necessarily have to have two branches), point B of the figure represents the bottomhole pressure log (shutdown or opened), which are obtained from the bottomhole sensor and through commercial software, the data corresponding to the entire test, is obtained; in this figure a computer and the resulting graph of the pressure data are represented. Point C corresponds to the EMELITRA®, which is connected to the discharge line from the well, the effluent is divided and flows through the ¼ "line that reaches the equipment of EMELITRA®, passes through the container, leaves the container and returns the fluid to the discharge line afterwards; EMELITRA®, wirelessly transmits the measurement (concentration) to the computer that has the software designed for such purposes installed, from which the real-time graphs (point E) of the measured data of the radioactive tracers in the effluent of the well are obtained (located a few meters from the well in this figure). Point D represents the collection of samples for chromatographic analysis, where a specialist takes the sample to the specified laboratory (located in the corresponding facilities). In this laboratory the sample is received and processed for the detection and quantification of the chemical tracers (partitionable and non-partitionable) of the spectrometers obtained in the chromatograph, through a software developed for this purpose, it is possible to visualize the graphs of the compounds of interest, in this figure represented by point F.

Figure 7:
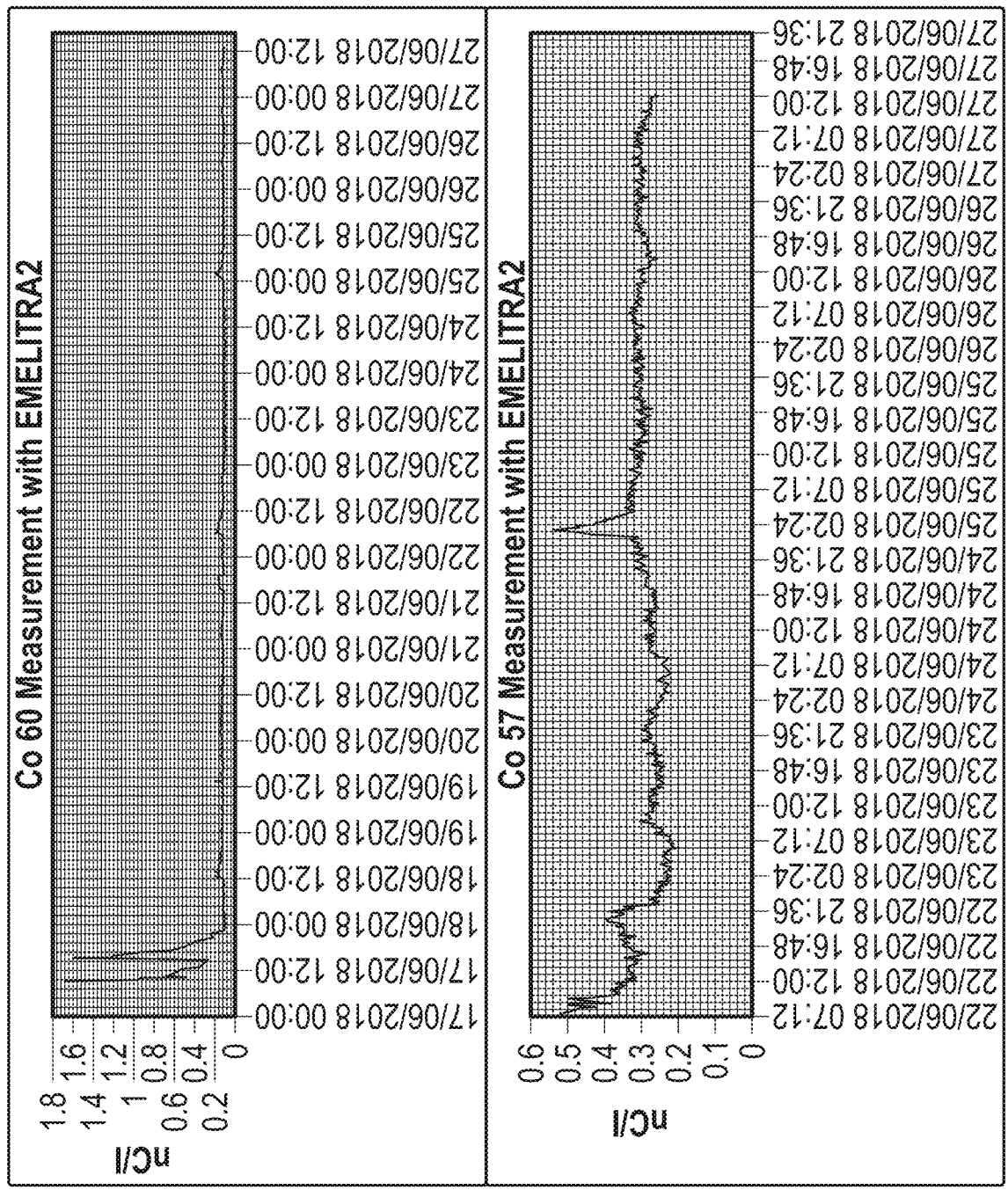

FIG. 7 shows the record obtained from the concentration measurements, both of cobalt 60 and cobalt 57, with EMELITRA®, during the entire time of the tracer test. The graphs presented here are obtained in real time, simultaneously as the well is producing. In this figure, it can be seen that the Co 60 graph begins on the day of the first production operation, while the Co57 graph starts on the date of the second production operation; Jun. 17, 2018 and Jun. 22, 2018, respectively as described in the example.

Figure 8:
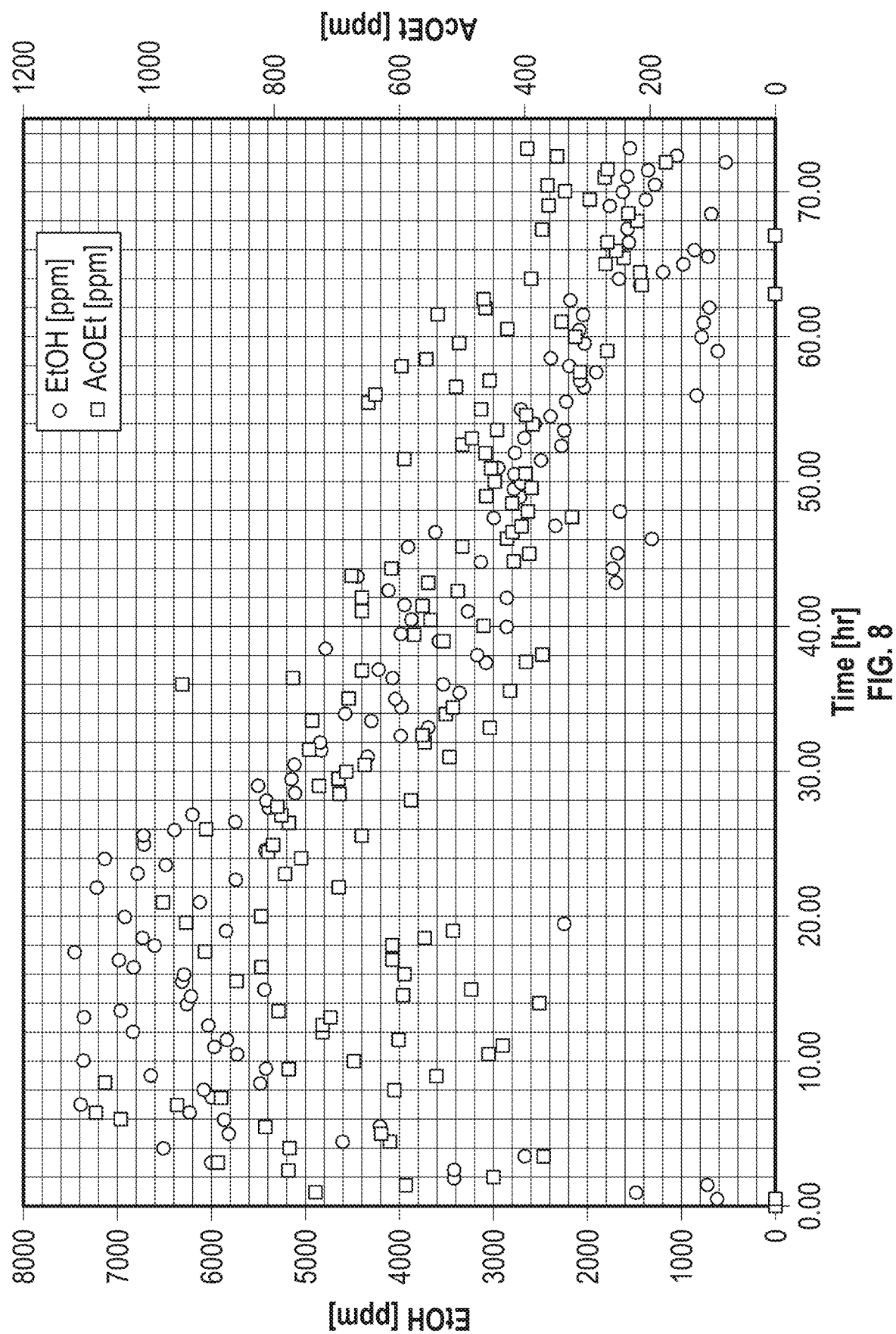

FIG. 8 presents the graph obtained from the data generated with the chromatographic analysis of all the samples collected. From here, the concentrations of both the primary tracer (ethyl acetate) and the secondary tracer (ethanol) are observed. The chromatography technique used is FID/GM, explained in the example.

Figure 9:
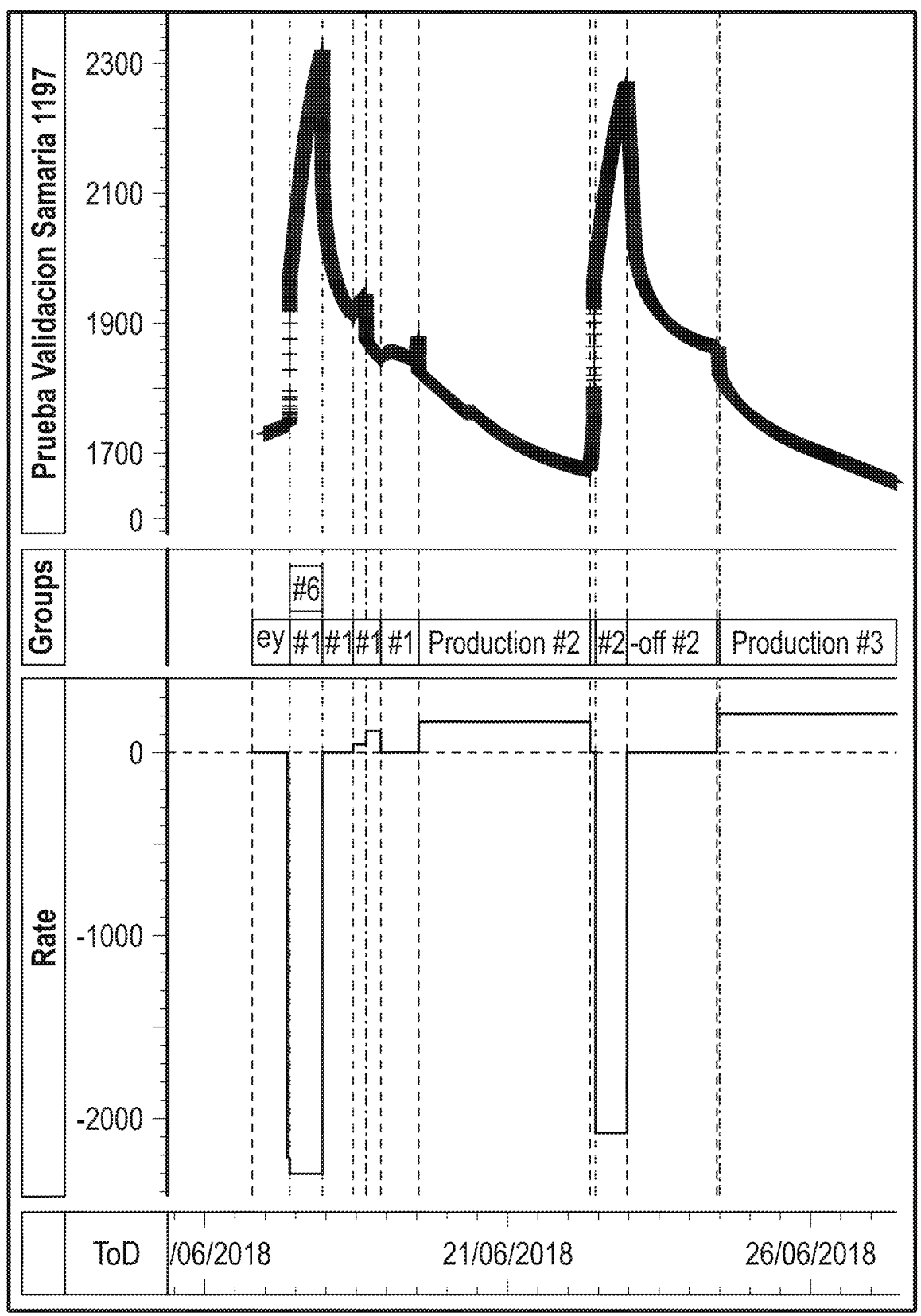

FIG. 9 shows the flowing bottomhole pressure log from the active well (upper graph) and the rates log (lower graph), obtained during the entire test set out in the example.

DETAILED DESCRIPTION OF THE DISCLOSURE

The present disclosure refers to a method that allows the user to estimate the remaining oil saturation in reservoirs, both naturally fractured and homogeneous, considering the participation of the matrix and present fractures. Measurement of the variation in the bottomhole pressure of the well itself and that of one or two observers is included. As well as, the formation of a reagent within the reservoir from the injection, obtaining at least two tracers in the formation, by means of a chemical reaction called hydrolysis.

For this method of the present invention, the use of tools is carried out, such as: Tracer Line measurement (EMELITRA®), Mexican patent MX346226 (B) by Jetzabeth Ramirez Sabag et al., incorporated by reference herein, which measures the concentration present in a well discharge line in real time; and, a laboratory that has the chromatographic analysis capacity for the compounds of interest, used for the detection and quantification of chemical tracers (TRAZAMOVIL®).

The present disclosure employs two types of tracers, radioactive and chemical; and pressure monitoring is also included in order to reduce substantially the uncertainty of chemical tracers' tests, and it combines additional technical elements that allow to reduce uncertainties, since it is a question of verifying the participation of the matrix and the present fractures, thereby achieving much greater assertiveness than conventional tracer tests and attributing to the reliability of the results of the test.

The method for estimating remaining oil saturation in naturally fractured reservoirs [Dual Tracer Pressure Monitoring Test, PDTcMP®] consists of three phases: the first two phases (I and II) are two tracers tests in a single well, each of them has three very similar periods: injection, shutdown and production of the well; and, the third phase, consists of the measurement (in the location of the well), of tracers concentrations injected in the fluids produced by the well, well discharge line and in real time, of the two previous phases. Continuously, six hours before the first injection, the bottomhole pressure and temperature are measured in the active well, as well as in the observer wells; the two Phases, Phase I and II, are two single well tracers tests.

Phase I. Non-partitionable tracer injection (radioactive). This phase consists of a mini tracer test (with radioactive tracer, gamma emission, non-partitionable) prior to the partitionable chemical tracer test (Phase II). This pre-test consists of three periods: injection, shutdown stand production, as follows:

I.1. Implantation of the non-partitionable tracer (any radioactive tracer, in this case Co60) in the formation, this as follows: a) injection of a formation water slug (optional), injection of a formation water slug with diluted radioactive tracer and injection of a formation water slug without tracer. I.2. Well shutdown (rest) for a certain time (24, 72 hours, for example). I.3. Well production (opening), with continuous measurement of bottomhole pressure (starts the test with pressure and temperature sensors installed in the involved wells, both active and observers), as well as continuous monitoring in real time of radioactive tracers' concentration in the discharge line of the well (this, provided by EMELITRA® which measures the concentration of the tracers and wirelessly transfers the information in real time to a computer equipment, located near the location of the well and based on the analysis of the tracers' breakthrough curves in real time, obtained by the verification of the injection rates, as well as the concentrations of the tracers.) The analysis of the tracer breakthrough curve is obtained in this phase, through the EMELITRA®, that is, the formation behavior is inferred, based on the tracer response measured in real time, that is, simultaneously as the reservoir fluids are produced in the well under study, with which, it is possible to know about the heterogeneities of the reservoir in the vicinity of the active well (around 6 to 20 m), and with this it is possible to prevent some problems of tracer return attributable to naturally fractured reservoirs (NFR).

In summary, this first phase is intended to investigate the formation into which the partitionable tracer will be injected and attempts to predict the response of the Phase II non-partitionable tracer. This mini-test significantly reduces the uncertainty in the response of the partitionable tracers. Once the mini-test has been performed and the tracer breakthrough curve analyzed, it is possible to infer with high certainty whether the program of the second test (partitionable tracers) is appropriate or requires modifications in order to run successfully.

Phase II. Injection of chemical tracers (partitionable and non-partitionable) with other radioactive tracer (non-partitionable). This phase also consists of three periods (similar to those of Phase I) injection, shutdown and production of the well; with the exception that the closing and production times are longer, this, to produce, where appropriate, the hydrolysis reaction with a known conversion, in such a way that allows the formation of the non-partitionable chemical tracer breakthrough curves. For the case of injecting a non-partitionable chemical tracer, there is no conversion restriction. The periods are as follows:

II.1. Simultaneous implantation of the partitionable tracer (ester, for example ethyl acetate and the radioactive gamma emission tracer (Co57, non-partitionable), as follows: a) injection of a formation water slug (optional), injection of a slug of formation water with partitioned chemical tracer diluted to 1-2% in the volume of water injected, and a simultaneous injection of the radioactive tracer used in the previous designed radioactive activity, and the injection of a slug of formation without a tracer, in order to move the slug carrying the tracers a few meters, II.2. Well shutdown (reaction time) for a certain time, specifically designed for the conversion given the hydrolysis reaction time of the tracer used. II.3. Well production, at a production rate. The entire phase with continuous measurement of bottomhole pressure (starts the test with the pressure and temperature sensors installed in the involved wells), as well as continuous real-time monitoring of the concentration of the radioactive tracer in the discharge line of the well (EMELITRA®). Injecting a partitionable (chemical) tracer and a non-partitionable tracer (Co57 radioactive, for example, different from Phase I).

The injection of Co57 purpose is to identify the injection water traced with ethyl acetate ester and to have a reference parameter with respect to the non-partitionable tracer (in this case, ethanol, product of the hydrolysis reaction). Likewise, by injecting the radioactive tracer Co57, simultaneously with the partitionable tracer (ethyl acetate), another innovative element is obtained to reduce uncertainty in tests of naturally fractured reservoirs.

Phase III. Detection and quantification of tracers at the location in real time. This phase consists of measuring the radioactive and chemical compounds of interest at the location of the well in real time. This is possible through the EMELITRA®, (radioactive tracers) and with the Laboratory for chromatographic analysis of the collected samples.

Additionally, it is highlighted that another innovative element of the present disclosure is to introduce tracer testing and continuous pressure monitoring during the test. Continuous measurement of pressure variation, using high resolution bottomhole pressure sensors in the wells involved, is included in the tracer test design. Two types of pressure responses are expected; the study of the well itself (active well) and that of some observer well, given that the tracer tests represent a series of pulses made to the formation. From the analysis and interpretation of these responses, some of the formation properties in the vicinity of the well could be determined, in order to have formation properties closer to the reality of the fractured porous medium and, if there is pressure interference between the wells (active and observer(s)), the compressibility of the formation could be determined, in addition to the established flow model, (very valuable information to integrate with the results of the tracer test). This data is expected to complement the information obtained with the tracer tests, in order to reduce the uncertainty generated by the complexity of the formation.

With the information obtained from the tracer test, a greater precision in the interpretation of both tests (tracers and pressure tests) is achieved. It should be clarified that the tracer test must be designed considering the possible pressure responses, simulated through the commercial software available, such as "Saphir" or "Pansystem", for example, and utilizing the available know properties in the vicinity of the well under study.

In summary, the test desing using the PDTcMP® to estimate the remaining oil saturation, substantially modifies the conventional tracer test with the innovative technical elements mentioned above, in order to reduce the uncertainty and/or ambiguity associated with naturally fractured reservoirs.

EXAMPLE. Next, an application example is cited that supports what has been described by the applicant, to determine the remaining saturation of fluids in naturally fractured and/or homogeneous reservoirs, without limiting the technical scope of the present invention. FIG. 6 presents the entire test process, point A of this figure corresponds to the active well; point B, the bottomhole pressure log; point C, corresponds to the well discharge line measurement equipment for radioactive tracers (EMELITRA®), in this case Co60 and Co57; the collection of the samples in the well and the corresponding shipment to the laboratory for the corresponding analysis of each one, is represented by point D; finally the points E and F of this figure show the tracers' breakthrough curves, radioactive and chemical, respectively.

The test was carried out in a field of a naturally fractured reservoir in the Gulf of Mexico, whose main characteristics of the well and the formation are the following: water invaded well, finished at the top of the Upper Cretaceous with a diameter of 5", in addition to a side track at a depth of 3107 md and with a maximum deviation angle of 21°, the well has two open intervals Ks1 and Ks2 at a depth of 4215 to 4232 md and 4291 to 4304 md respectively. Two continuous pneumatic pumping valves are installed in its production rig at a depth of 2954 md and 3899 md. The recorded bottomhole temperature is 135° C. and a flowing bottomhole pressure of 1650 psi. The liquid level is 3600 md, the type of oil produced is light of 28° API and congenital water with salinity of 87,000 ppm. The well is located in a formation corresponding to a naturally fractured area and is mainly made up of limestones with low percentage of clay and dolomite intercalations, and an average permeability of the study area is 8 mdarcy and the average porosity 0.08%.

Figure 1A:
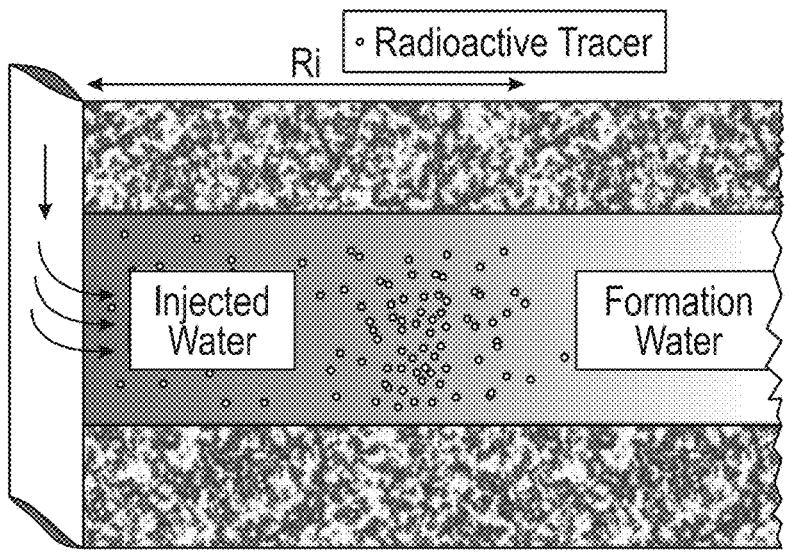
Figure 1B:
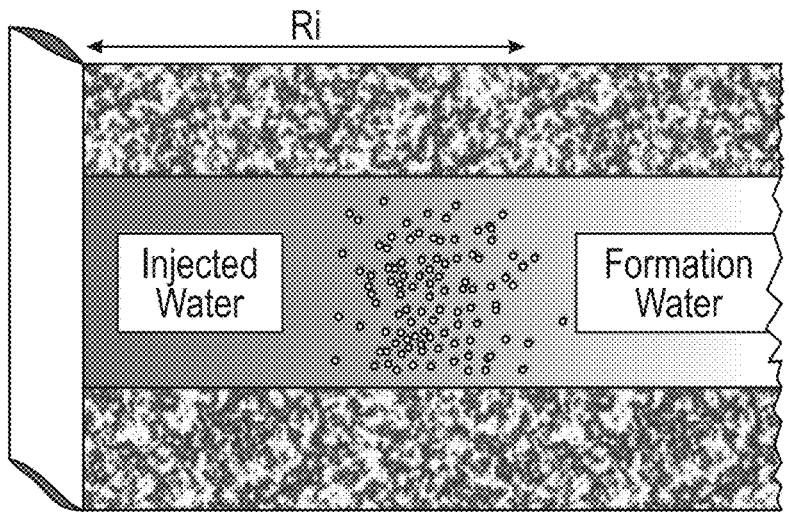
Figure 1C:
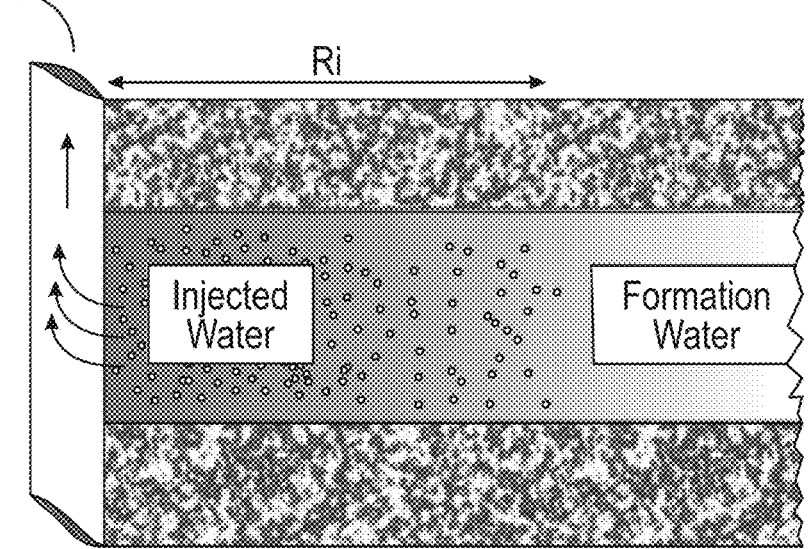
Figure 2:
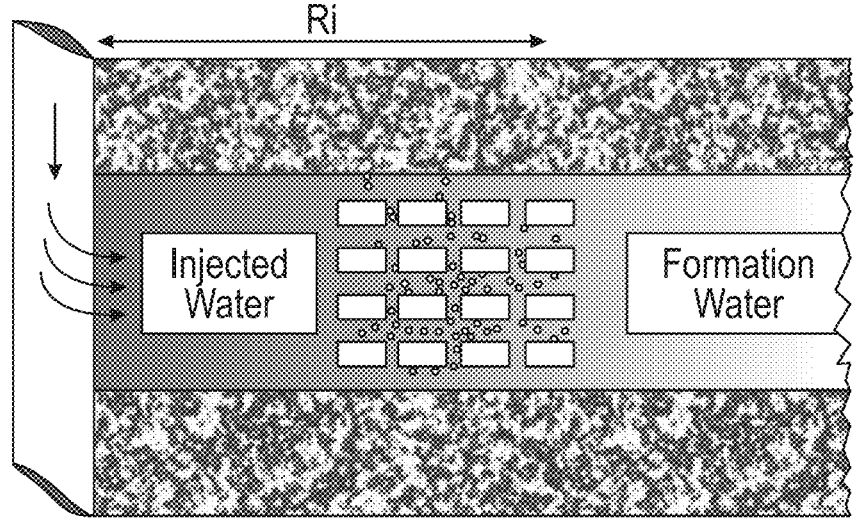
FIG. 2 illustrates a schematic representation of the partitionable tracer injection, selecting any ester tracer, where: RI represents the radius of investigation of the procedure.
Figure 3:
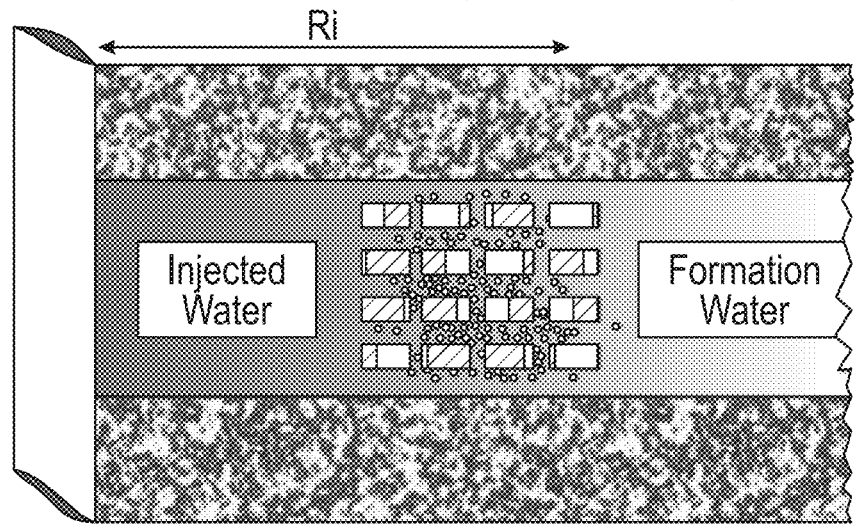
FIG. 3 shows the closing period for a chemical reaction (hydrolysis) to occur with the primary tracer, and for the secondary tracer to occur in situ (may be ethanol or isopropanol, etc., depending on the ester injected as primary).
Figure 4:
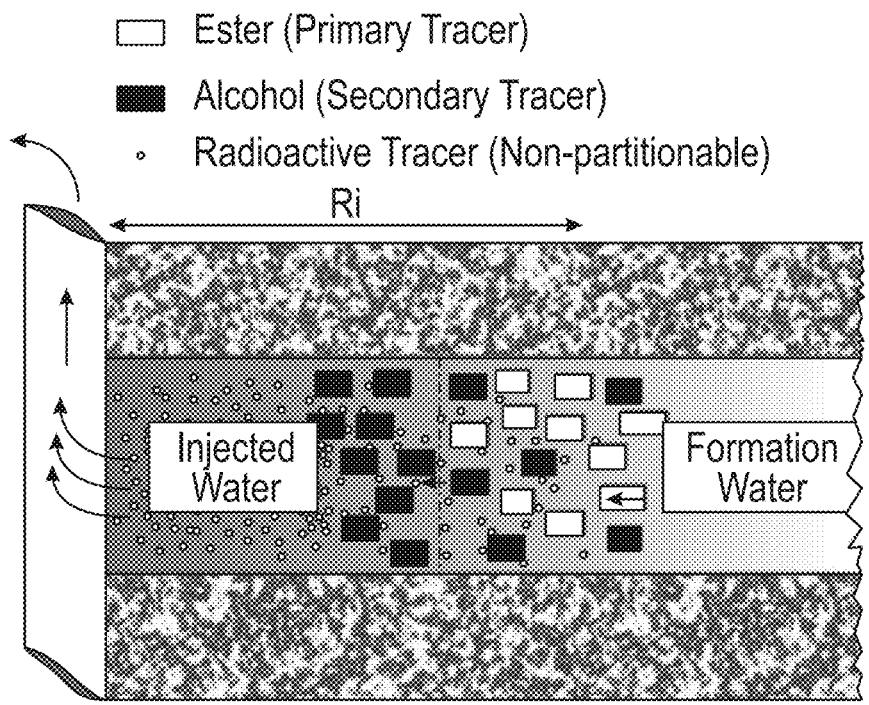
FIG. 4 shows the production period after shutdown, the displaced formation water is shown and as a result of the chemical reaction (hydrolysis) the second tracer or secondary tracer is observed, represented by rectangles.

PDTcMP® system test performed consisted of the following: two phases: a) A mini-tracer test with the radioactive tracer Co60, see FIG. 1 (injection, point A, shutdown, point B and production, point C), with the production monitored with EMELITRA®, in order to measure in real time the concentration of the tracer Co 60 in the discharge line, and thereby obtain the Co60 breakthrough curve (FIG. 7, upper graph); and b) a test of chemical tracers (partitionable) with the simultaneous injection of a radioactive tracer different from the one used in the mini-test (subsection b of FIG. 1) Co57 in this case, in the injection of two radioactive tracers of gamma emission (see FIG. 2) and a chemical tracer in the target formation (see FIG. 2). The shutdown period, in order to achieve a reaction, is represented in FIG. 3 with the continuous monitoring of the two injected radioactive tracers (as well as two chemical tracers, the primary one that was injected and the secondary one, which is the product of the hydrolysis reaction carried out in the formation). FIG. 4 corresponds to the production stage of Phase II of the test carried out. In this Figure it is possible to observe the tracer esters of this stage: primary, secondary and radioactive tracer.

The hypothetical chemical tracers' breakthrough curves are presented in FIG. 5. In this figure the response of the primary tracer (in this case, ethyl acetate) represented by the letter a, and the secondary tracer, in this case ethanol, can be seen, so the breakthrough curves will be the curves represented by the letters a and b of this figure. Also, the axis of the abscissa is the volume produced in the study well, (which corresponds implicitly to the time), so that, approximately, these curves indicate the maximum peak of the tracers (Qa and Qb). In this graph, the volumes produced are, Va and Vb, of the primary and secondary tracers, respectively. The letters K and J correspond to the axes corresponding to those of the concentrations of the tracers, primary and secondary.

The development of the test is divided into two Phases: the first Phase began with the injection of 1500 bbl of congenital water and Cobalt 60 with an initial concentration of 0.01677 µCi/l with a total activity of 4 mCi, and an injection rate of 2 bbl/min, ending with the injection of 135 bbl of congenital water at the same rate as the previous injection. At the end of the injection stage, the well was shut down for 38 hours, as part of the resting stage, and later opened to production with the aid of a continuous pneumatic pump installed in the well. The well-produced for 66 hours, obtaining a total recovered volume of liquid 956.06 barrels (908.8 bbl corresponding to water and 47.26 bbl to oil). The production rate was, on average, 351.5 bbl/day.

During the production stage of Phase I, the real-time detection and quantification of Cobalt 60 was performed with EMELITRA®, programmed to obtain data every 15 minutes. The equipment presented an average acquisition error data of 0.00337, which represents an average effectiveness of 99.48%. According to data measured by EMELITRA®, during this production phase, 0.364 mCi of Cobalt 60 was recovered, as shown in FIG. 7.

Based on the analysis of the results of the first phase and the data measured in real time, the decision to continue with phase II of the test with the following changes to the original design was made: a) eliminate the programmed water slug to start the second phase; b) decrease the volume of injection water and the injection rate; c) increase the concentration of ethyl acetate and d) decrease the shutdown period (or reaction time). That is, according to the method of the present invention, the design of the test based on the first phase of the same was optimized, in order to guarantee the success of the second phase.

Given the above, the second phase began by supplying the injection of 1,300 bbl of congenital water, Ethyl Acetate and Co 57 diluted with a concentration of 2.4% v/v and Cobalt 57 with a total activity of 20 mCi, at a cost of 1.8 bbl/min, followed by the injection of a 135 bbl congenital water slug, maintaining the same injection rate of 1.8 bbl/min. The well was shut down for 36 hours and opened again to produce during a period of 72.5 hours, obtaining a total recovered volume of liquid of 1279.2 bbl (1246.40 bbl of water and 33.42 bbl of oil), and producing at an average rate of 426.6 bbl/day. At the end of the production period, the well was shut down again, terminating Phase II.

During the production of Phase II, real-time detection and quantification of Cobalt 57, injected at the beginning of this phase, and Cobalt 60, injected during the first phase, were performed by EMELITRA®, with a measurement interval programmed to be each 15 minutes to obtain radioactive activity. A recovery of 0.125 mCi of Cobalt 57 was obtained during this production phase, as observed in FIG. 7. The analysis of the samples lasted 24 hours, with a detection and quantification process of 4 extractions per sample, the determination of the 4 vials of each sample is obtained in one hour, which is why the analysis is achieved in real time with a lag of one hour. The analysis of the samples was completed at the expected times. Sampling was carried out according to the program, it was carried out with a frequency of 30 minutes during the 72.5 hours of production of Phase II and 145 samples were collected, which were treated in the Laboratory, measuring salinity, pH, conductivity, water separation oil and quantifying the tracer concentration by gas chromatography. According to the material balance, 41% of the injected chemical tracer (ethyl acetate and its derivatives) was recovered. FIG. 8 shows the breakthrough curves of the primary (ethyl acetate) and secondary (ethanol) tracers, constituted by the data obtained from the chromatographic analysis of the 145 samples collected.

In relation to another innovative element of this disclosure, pressure monitoring, as already mentioned, continuously monitors the background pressure, starting six hours before the first injection (Phase I), and thorough the entirety of the test (Phases I and II). The following explains how the main pressure variation events were constituted, which consisted of 8 main events in which the pressure was monitored with a memory probe backed up to 4175 [m] in the active well: Phase I, I. 1) First injection of radioactive tracer=First injection test, I.2) First well shutdown (rest or reaction)=first fall-off test, I.3) First production=first drawdown test, well closure (questions operating)=first buildup test; continuous first production=second drawdown test of Phase 1; Phase II: II.1) Second Injection (chemical and radioactive tracer)=Second Injection test, II.2) Second well shutdown (second rest or reaction)=Second fall-off test; and finally II.3) Second production and first sampling of fluids for chromatographic analysis=Second drawdown test. Below is the figure of the closed-bottomhole or flowing pressure log (BHPC or F), according to each event (using the software). FIG. 9, presents two graphs; the upper graph, corresponding to the bottom hole pressure log, flowing or closed (as the case may be) against time, of all the events mentioned above; and the lower graph corresponding to the injection, shutdown, production, injection, shutdown and production events of the active well.

Stages of the Technological Test with "Saphir" software. The pressure data measured by the sensor located at a depth of 4175 [m] were calculated at the interval using the RPFC performed during the descent of the tool.

Based on the results obtained, analyzed and interpreted from the pressure events defined above, and based on the relative permeability curves of the field under study, it is estimated that there is a probability of 52% of them are within the range of 0.27 to 0.44 water saturation and 76% of the results indicate that the oil saturation is between 0.20 to 0.30 with an oil displacement value of 0.02. It is highlighted that it was carried out according to the operational program proposed in the protocol; likewise, it is pointed out that throughout the the test, all the safety protocols required by the Safety and Risk System were followed and complied with.

The validation of the test design is verified using the following criteria:

1. Obtaining data that are consistent with the expected response, allowing estimation of the remaining oil saturation in a naturally fractured reservoir.

The data obtained from the tracer response, monitored on the surface in real time (2 radioactive and 2 chemical), were consistent according to the expected response. This is demonstrated with the breakthrough curve obtained and with the recovery of the tracers. It should be noted that, the design of the test, was based on the results obtained from the study of dynamic reservoir evaluation and all the predictions made, both with mathematical models and with numerical simulation using the previously estimated values of the parameters involved. In fact, the above is part of the methodology developed by this author. Hence, the tracer responses were strong despite being a naturally fractured deposit. In this case, it was possible to obtain a very significant and important recovery of the tracers, particularly during the mini-test (first phase of the technological test, where 41% of the injected tracer was recovered). During the production of the second phase, 30.1% of Co57, 37% of ethyl acetate, and 28% of Co60 (injected in the first phase), were also recovered.

The tracers' breakthrough curves allow, through different methods, the calculation of the remaining oil saturation, despite being a naturally fractured reservoir, it is also noted that the production of oil, even with the amount of water injected, is evidence of the matrix contribution to the production. This is also corroborated with the mixture of the injected water 70,000 ppm and the formation water 40,000 ppm.

2. The validation of the technique used to interpret the test results and estimate the remaining oil saturation will be verified by:

The consistency of the calculated ROS values. As already mentioned, the estimation of the remaining oil saturation was consistent with the tracer methods themselves, and there is also consistency with the results of the estimations of other techniques, such as those of material balance, production data, numerical simulation and pressure testing technique.

It should be noted that the test design was based on the results obtained from the dynamic reservoir evaluation study and all the predictions made, both with mathematical models and with numerical simulation using the previously estimated values of the parameters involved. In fact, the above is part of the methodology developed by this author. Hence, the tracer responses were overwhelming despite being a naturally fractured deposit.

The design of the PDTcMP® offers the following benefits:

This test allows the estimation of the remaining oil saturation, considering the participation of both, matrix and fracture.

Reduces the uncertainty associated with fractured formations.

It is a totally innovative tracer test, designed to estimate residual/remaining oil saturation in naturally fractures reservoirs, which is a significant contribution, since conventional tests are successful in reservoirs with homogeneous behavior.

Two types of tracers are used; radioactive and chemical, in addition to the monitoring of pressure, both in the active well and in the observers, in order to substantially reduce the uncertainty of the tests that exclusively use chemical tracers.

The proposed procedure contains additional technical elements that allow us to reduce uncertainties, since it is a matter of verifying the matrix and fracture participations.

Additional techniques to the traditional are considered, thereby achieving much greater assertiveness than the conventional tracer tests applied to fractured reservoirs.

When carrying out the mini-test and analyzing the tracer breakthrough curve, it is possible to infer with certainty, if the design of the second test, the one with partitionable tracers; is appropriate or requires modifications, so that the main aspects that need to be taken care of are covered in order to run a successful test.

Both, radioactive tracers and pressure logs, are the elements that set apart this invention from conventional tests, so that with the use of these new elements, incorporated in this procedure, it is possible to syncretize this participation.

The invention claimed is:

1. An operational method for a system to determine the remaining saturation of existing fluids in naturally fractured and/or homogeneous reservoirs, comprising:
   I) injection of non-partitionable tracer (radioactive);
   II) simultaneous injection of chemical tracers (partitionable and non-partitionable) and an injection of a radioactive tracer different from that of the previous phase; and
   III) detection and quantification of concentrations of the tracers in a location of the well in real time;
   wherein the system comprises:
      an active oil well head, under study;
      a pressure and temperature sensor with a high background resolution; and
      a continuous and real-time measurement of the radioactive tracer concentration in a well discharge line.

2. The method for the operation of the system of claim 1, wherein the Phase I injection of non-partitionable tracer (radioactive) further comprises:
   a) the injection at constant rate of the mixture of formation water with radioactive tracer (non-partitionable) diluted from about 0.5% to about 3%;
   b) displacement of a slug of a) with formation water, without tracer,
   c) shutdown of the well; and
   d) production of the same well at a ½ the rate of the injection rate of Phase I, subsection a), for a time approximately 3 times the injection time; and
   e) measurement of the well discharge line in real time of the concentration of the tracer produced.

3. The method for the operation of the system of claim 1, wherein Phase II further comprises the simultaneous injection of a partitionable tracer (chemical) and a non-partitionable tracer (radioactive), different from that of Phase I.

4. The method for the operation of the system of claim 1, wherein Phase III further comprises measurement of the tracers produced in the well under study, both radioactive and chemical in the location of the well in real time.

5. The method for the operation of the system of claim 1, wherein a variation in a bottomhole pressure of the well under study is measured from a series of pulses produced in the formation, allowing the uncertainty to be reduced by an amount in a range of approximately 20% to about 50% in the characterization of naturally fractured and homogeneous reservoirs.

6. The method for the operation of the system of claim 1, wherein the tracer is a radioactive beta or gamma emission isotope, or a chemical.

7. The method for the operation of the system of claim 1, wherein the partitionable tracer is a chemical compound that reacts with remaining water in the formation.

8. The method for the operation of the system of claim 1, wherein an injection, shutdown and production are presented at design times of two types of tracers, both radioactive and chemical.

9. The method for the operation of the system of claim 1, wherein an estimation of a remaining oil saturation in a matrix of naturally fractionated reservoirs is about 25% to about 80% of the total oil remaining in the formation.

10. The method for the operation of the system of claim 1, wherein an estimation of a remaining oil saturation in a matrix of naturally fractionated reservoirs is about 25% to about 80% of the total remaining volume and wherein, for the case of homogeneous deposits, an oil saturation value of about 0.1 to about 0.30 is obtained for the rock fluid system.

11. The method for the operation of the system of claim 1, wherein an alcohol is obtained after a chemical reaction of hydrolysis.

12. The method for the operation of the system of claim 1, wherein the tracer formed is a non-partitionable alcohol.

13. The method for the operation of the system of claim 1, wherein the radioactive beta or gamma emission isotope is selected from a group consisting of Co60 and Co57, and the chemical is selected from a group consisting of ethyl acetate and propyl acetate.

* * * * *